United States Patent
Nozato

(10) Patent No.: US 8,646,915 B2
(45) Date of Patent: Feb. 11, 2014

(54) OPHTHALMIC APPARATUS, CONTROL METHOD FOR THE SAME, AND STORAGE MEDIUM

(75) Inventor: Koji Nozato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/177,715

(22) Filed: Jul. 7, 2011

(65) Prior Publication Data

US 2012/0019780 A1    Jan. 26, 2012

(30) Foreign Application Priority Data

Jul. 23, 2010   (JP) .................................. 2010-166502

(51) Int. Cl.
*A61B 3/10* (2006.01)
*A61B 3/00* (2006.01)

(52) U.S. Cl.
USPC ............ 351/221; 351/200; 351/205; 351/211

(58) Field of Classification Search
USPC .......... 351/206, 200, 203, 205, 210–211, 221
See application file for complete search history.

(56) References Cited

U.S. PATENT DOCUMENTS

| | | | |
|---|---|---|---|
| 4,213,678 A | 7/1980 | Pomerantzeff et al. | |
| 5,321,501 A | 6/1994 | Swanson et al. | |
| 6,137,585 A | 10/2000 | Hitzenberger et al. | |
| 6,288,784 B1 | 9/2001 | Hitzenberger et al. | |
| 6,331,059 B1 | 12/2001 | Kudryashov et al. | |
| 6,648,473 B2 | 11/2003 | DellaVecchia et al. | |
| 7,311,402 B2 * | 12/2007 | Mihashi et al. | 351/221 |
| 7,367,672 B2 | 5/2008 | Akita | |
| 7,466,423 B2 | 12/2008 | Podoleanu et al. | |
| 7,677,731 B2 | 3/2010 | Mihashi et al. | |
| 2002/0172253 A1* | 11/2002 | Vetrovec | 372/95 |
| 2005/0045801 A1* | 3/2005 | Smith | 250/201.9 |
| 2005/0073647 A1 | 4/2005 | Mihashi et al. | |
| 2005/0110948 A1* | 5/2005 | Bille | 351/206 |
| 2007/0010313 A1 | 1/2007 | Akita | |
| 2007/0046948 A1* | 3/2007 | Podoleanu et al. | 356/497 |
| 2008/0033301 A1* | 2/2008 | DellaVecchia et al. | 600/477 |
| 2008/0123053 A1 | 5/2008 | Mihashi et al. | |
| 2010/0166293 A1 | 7/2010 | Sugita et al. | |

FOREIGN PATENT DOCUMENTS

| | | |
|---|---|---|
| JP | 2002-515593 A | 5/2002 |
| WO | 99/60331 A1 | 11/1999 |
| WO | 03/022138 A1 | 3/2003 |
| WO | 2011/061896 A1 | 5/2011 |

OTHER PUBLICATIONS

Communication dated Nov. 25, 2011, forwarding a European Search Report dated Nov. 18, 2011, in European Application No. 11174888.5-1265.
Handbook of Optical Coherence Tomography (2006) (pp. 145, 149, Figs. 2, 3; p. 338, Fig. 1).
Y. Zhang et al., High-speed volumetric imaging of cone photoreceptors with adaptive optics spectral-domain optical coherence tomography, Optics Express, vol. 14, No. 10, pp. 4380-4394, May 15, 2006.
Sep. 9, 2013 Chinese Official Action in Chinese Patent Appln. No. 201110209371.7.

* cited by examiner

*Primary Examiner* — Dawayne A Pinkney
(74) *Attorney, Agent, or Firm* — Fitzpatrick, Cella, Harper & Scinto

(57) ABSTRACT

An ophthalmic apparatus comprises: aberration correction unit arranged to correct aberration of at least one of irradiating light directed to an eye to be examined and return light from the eye; light-receiving unit arranged to receive, as return light from the eye, the light whose aberration is corrected by the aberration correction unit and then which irradiates the eye; measurement unit arranged to measure the aberration of the return light; and control unit arranged to control the aberration correction unit based on a measurement result obtained by the measurement unit and a light reception result obtained by the light-receiving unit.

15 Claims, 8 Drawing Sheets

F I G. 3A
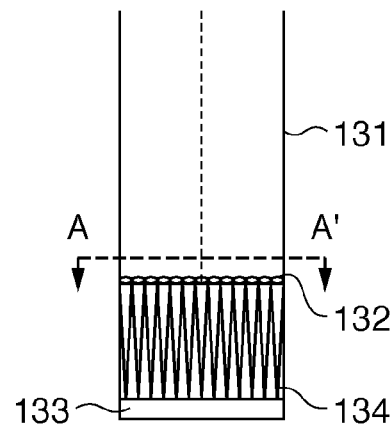
F I G. 3B
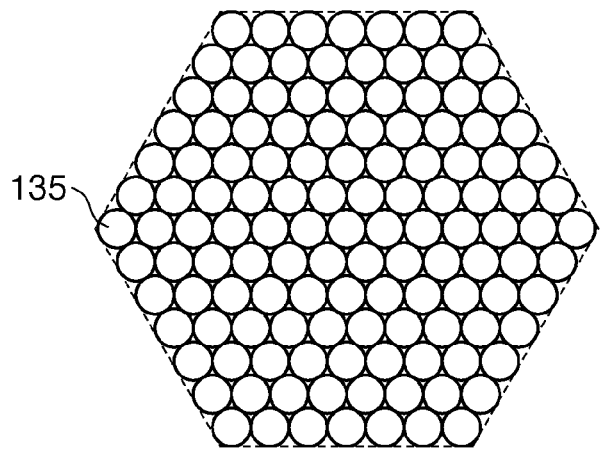
F I G. 3C
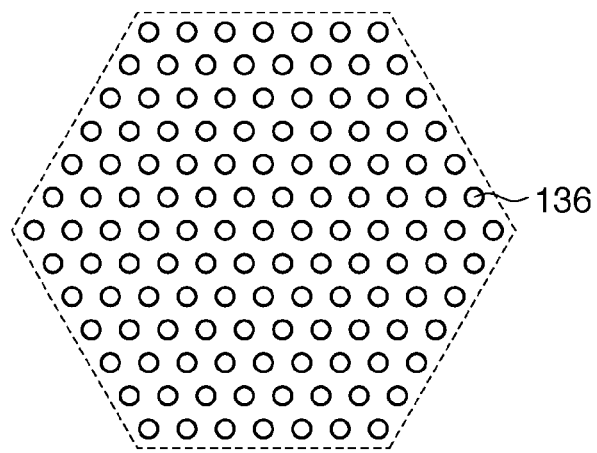

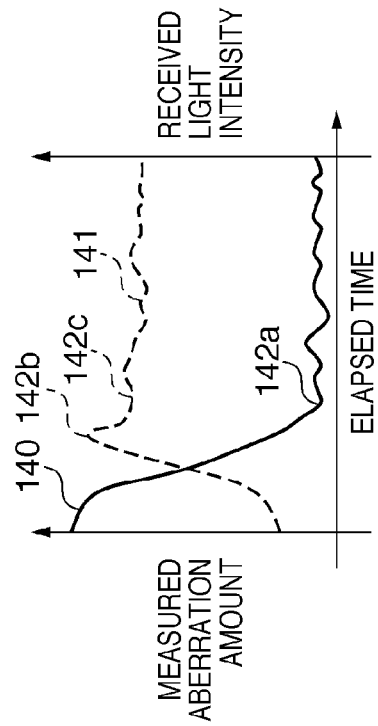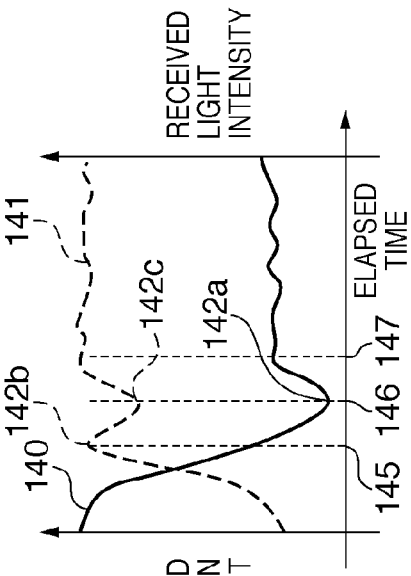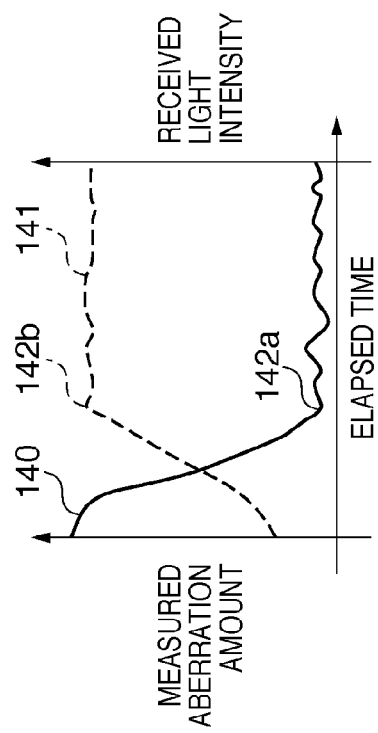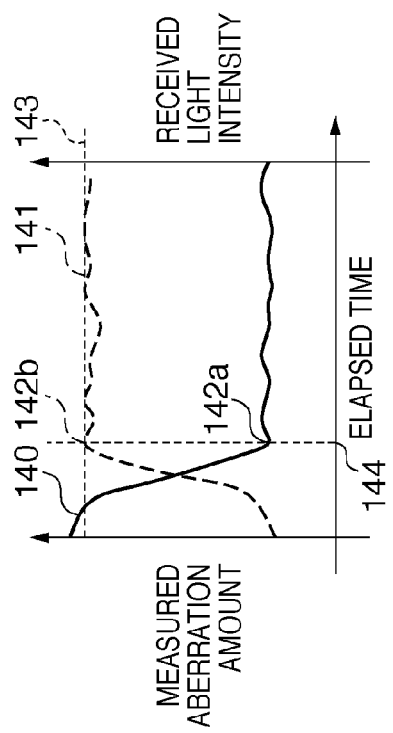

OPHTHALMIC APPARATUS, CONTROL METHOD FOR THE SAME, AND STORAGE MEDIUM

BACKGROUND OF THE INVENTION

1. Field of the Invention

The present invention relates to an ophthalmic apparatus, a control method for the apparatus, and a storage medium and, more particularly, to an ophthalmic apparatus which has an adaptive optical function of measuring and correcting the aberration of an eye to be examined and can correct the aberration in accordance with imaging states, a control method for the apparatus, and a storage medium.

2. Description of the Related Art

Recently, as an ophthalmic imaging apparatus, an SLO (Scanning Laser Ophthalmoscope) apparatus like the one disclosed in U.S. Pat. No. 4,213,678 has been widely used, which two-dimensionally irradiates the fundus with a laser beam and receives the reflected light.

In addition, an imaging apparatus using low-coherence light interference has been put into practice. This apparatus is called OCT (Optical Coherence Tomography), which is used in the field of ophthalmology, in particular, to obtain a tomogram of the fundus or its neighboring region. As a type of OCT, there is available a method called TD-OCT (Time Domain OCT) disclosed in U.S. Pat. No. 5,321,501 or Japanese Patent Laid-Open No. 2002-515593. As another type of OCT, a method called SD-OCT (Spectral Domain OCT) is disclosed in Handbook of Optical Coherence Tomography (2006) (pp. 145, 149, FIGS. 2, 3; p. 338, FIG. 1).

Such an ophthalmic imaging apparatus has recently been improved in resolution by, for example, increasing the NA of a laser irradiation optical system. When, however, imaging the fundus, it is necessary to perform imaging through the optical tissue of the eye, such as the cornea and crystalline lens. With an increase in resolution, the aberration of the cornea and crystalline lens has greatly influenced the image quality of captured images. Under the circumstances, studies have been conducted on AO (Adaptive Optics)-SLO and AO-OCT incorporating, in an optical system, AO which measures and corrects the aberration of the eye. AO-OCT is disclosed in, for example, Y. Zhang et al., Optics Express, Vol. 14, No. 10, 15 May 2006. AO-SLO and AO-OCT generally measure the wavefront of the eye by the Shack-Hartmann wavefront sensor system. The Shack-Hartmann wavefront sensor system is a technique of measuring the wavefront of the eye by irradiating the eye with measurement light and making a CCD camera receive the reflected light through a microlens array. It is possible to perform high-resolution imaging by driving wavefront correction devices such as a deformable mirror and a spatial phase modulator so as to correct a measured wavefront, and imaging the fundus through the devices.

A fundus imaging apparatus including the above conventional adaptive optical system is generally configured to keep a light-receiving unit for reflected light and a wavefront sensor in an optically conjugate relation so as to allow the wavefront sensor to measure aberration similar to the aberration state at the light-receiving unit. In many cases, such apparatuses perform feedback control, that is, repeatedly driving the wavefront correction devices based on the information measured by the wavefront sensor. The reason for feedback control is to cope with errors between instruction values and actual correction amounts and variations in aberration depending on the states of the tear fluid and refractive adjustment of the eye.

In this arrangement, it should be able to reduce the aberration of signal light at the light-receiving unit and improve the light reception efficiency by reducing the aberration using the wavefront sensor. Even if, however, the aberration measured by the wavefront sensor becomes minimum, the light reception efficiency may not become maximum depending on the influences of measurement errors in the wavefront sensor due to the influence of stray light, aberration existing in the optical system of the light-receiving unit such as a collimator, and disturbance in the conjugate relation between the wavefront sensor and the light-receiving unit.

It may be possible to cope with disturbance in the conjugate relation between the wavefront sensor and the light-receiving unit and aberration in the light-receiving unit by performing detection, adjustment, and the like at the time of assembly of the apparatus. However, it is very difficult to cope with the influence of stray light to the wavefront sensor because it is difficult to predict it in advance. Even if it is possible to cope with this, it is necessary to change aberration correction control depending on individual differences among apparatuses and installation conditions. This imposes a very heavy load in terms of apparatus adjustment.

In consideration of the above problems, the present invention provides a technique which allows the performance of aberration correction in accordance with imaging states and the performance of imaging with high image quality.

SUMMARY OF THE INVENTION

According to the first aspect of the present invention, there is provided an ophthalmic apparatus comprising: aberration correction unit arranged to correct aberration of at least one of irradiating light directed to an eye to be examined and return light from the eye; light-receiving unit arranged to receive, as return light from the eye, the light whose aberration is corrected by the aberration correction unit and then which irradiates the eye; measurement unit arranged to measure the aberration of the return light; and control unit arranged to control the aberration correction unit based on a measurement result obtained by the measurement unit and a light reception result obtained by the light-receiving unit.

According to the second aspect of the present invention, there is provided a control method for an ophthalmic apparatus, the method comprising: an aberration correction step of correcting aberration of at least one of irradiating light directed to an eye to be examined and return light from the eye; a light-receiving step of receiving, as return light from the eye, the light whose aberration is corrected in the aberration correction step and then which irradiates the eye; a measurement step of measuring the aberration of the return light; and a control step of controlling a aberration correction step based on a measurement result obtained in a measurement step and a light reception result obtained in the light-receiving step.

Further features of the present invention will be apparent from the following description of exemplary embodiments with reference to the attached drawings.

BRIEF DESCRIPTION OF THE DRAWINGS

FIG. 3A is a view showing the arrangement of a wavefront sensor;

FIG. 3B is a view showing the arrangement of the wavefront sensor when observed from the A-A direction;

FIG. 3C is a view showing an example of the measurement result obtained by the wavefront sensor;

FIG. 6A is a graph showing changes in measured aberration amount and received light intensity in an apparatus having an aberration correction function in an ideal state;

FIG. 6B is a graph showing an example of changes in aberration amount and received light intensity in an apparatus having a general aberration correction function;

FIG. 6C is a graph showing changes in measured aberration amount and received light intensity according to the first embodiment;

FIG. 6D is a graph showing changes in measured aberration amount and received light intensity according to the second embodiment;

DESCRIPTION OF THE EMBODIMENTS

Figure 1:
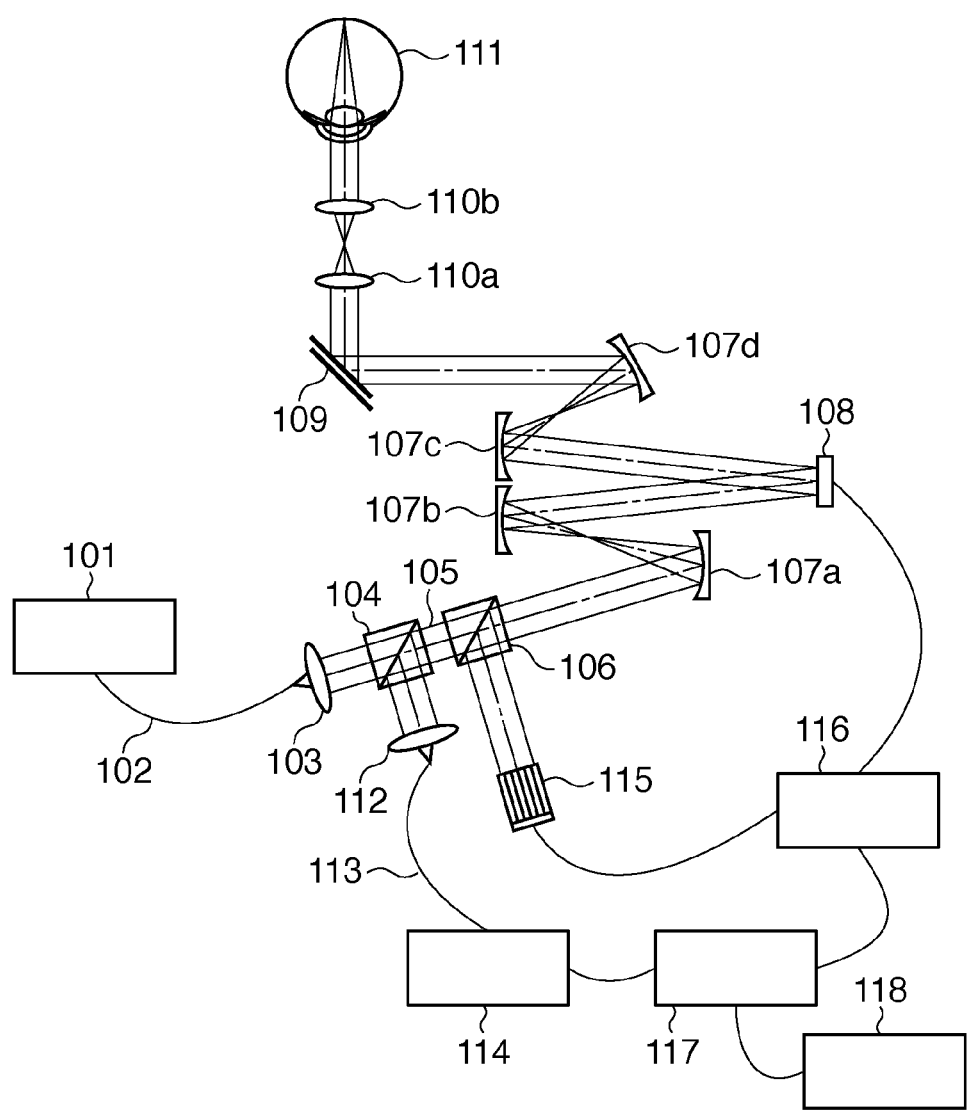
FIG. 1 is a view for explaining a Scanning Laser Ophthalmoscope (SLO) in this embodiment.

Embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

(First Embodiment)

An embodiment of the present invention will be described in detail below with reference to the accompanying drawings. An example of a fundus imaging apparatus according to the present invention will be described first with reference to FIG. 1. The following is an example of a scanning laser ophthalmoscope (SLO) with an adaptive optical function.

The light source 101 is an SLD (Super Luminescent Diode) light source with a wavelength of 840 nm. The wavelength of the light source 101 for fundus imaging is preferably about 800 nm to 1,500 nm to reduce glare for an object to be examined and maintain a high resolution. Although this embodiment uses an SLD light source, it is possible to use a laser or the like. In addition, the embodiment uses the single light source for fundus imaging and wavefront measurement. However, it is possible to use different light sources for the respective operations or perform optical multiplexing on the way.

A collimator 103 collimates light emitted from the light source 101 through a single-mode optical fiber 102, and outputs it as collimated measurement light 105. The output measurement light 105 is transmitted through a light splitting unit 104 including a beam splitter, and is guided to an adaptive optical system.

The adaptive optical system includes a light splitting unit 106, a wavefront sensor 115, a wavefront correction device 108, and reflecting mirrors 107a to 107d for guiding light to them. In this case, the reflecting mirrors 107a to 107d are arranged to set at least the pupil of the eye, the wavefront sensor 115, the wavefront correction device 108, and a collimator 112 for the reception of measurement light in an optically conjugate relation. This embodiment uses, for example, a beam splitter as the light splitting unit 106.

The measurement light 105 transmitted through the light splitting unit 106 strikes the wavefront correction device 108 via the mirrors 107a and 107b. The measurement light 105 reflected by the wavefront correction device 108 emerges to the reflecting mirror 107c. The wavefront correction device 108 is a correction device capable of correcting the aberration of the eye to be examined. As the wavefront correction device 108, it is possible to use, for example, a spatial phase modulator using a liquid crystal element.

Figure 2A:
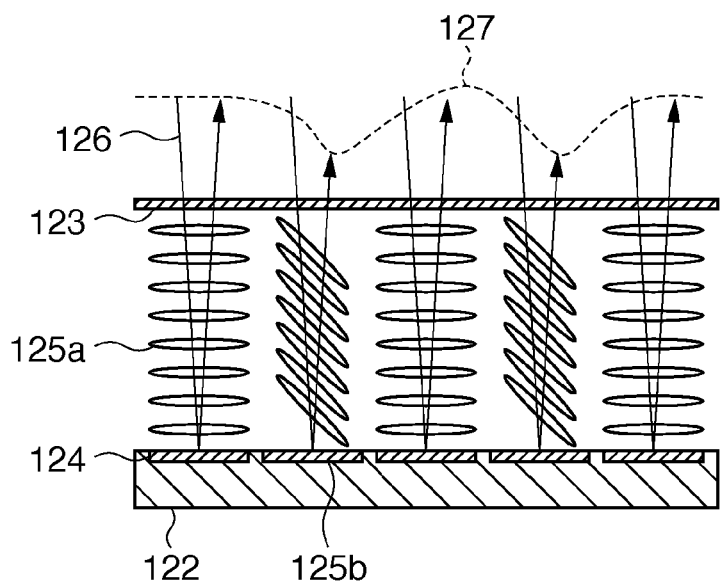
FIG. 2A is a view showing the arrangement of a phase modulator.

An example of the arrangement of a reflection type liquid crystal optical modulator as an example of a spatial phase modulator will be described with reference to FIG. 2A. This reflection type liquid crystal optical modulator has a structure in which liquid crystal molecules 125 are sealed in the space between a base portion 122 and a cover 123. The base portion 122 includes a plurality of pixel electrodes 124. The cover 123 includes a transparent counter electrode (not shown). When no voltage is applied between the electrodes, the liquid crystal molecules 125 are aligned like liquid crystal molecules 125a. When a voltage is applied, the liquid crystal molecules 125 shift to the aligned state of liquid crystal molecules 125b. This changes the refractive index for incident light 126. Changing the refractive index of each pixel by controlling a voltage to each pixel electrode can perform spatial phase modulation. When, for example, the incident light 126 strikes the liquid crystal element, the incident light 126 passing through the liquid crystal molecules 125b retards in phase relative to the incident light 126 passing through the liquid crystal molecules 125a. As a result, a wavefront 127 like that shown in FIG. 2A is formed. In general, the reflection type liquid crystal optical modulator includes several tens of thousands (10,000) to several hundreds of thousands (100,000) of pixels.

In addition, the liquid crystal element has a polarization property, and hence includes a polarization element for adjusting the polarization of the incident light 126.

Figure 2B:
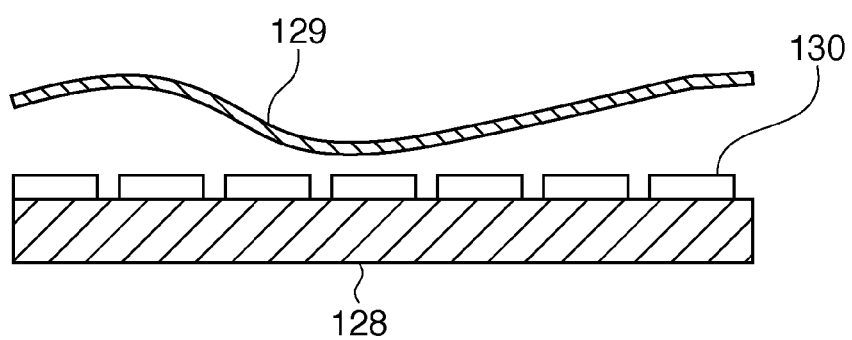
FIG. 2B is a view for explaining a deformable mirror.

Another example of the wavefront correction device 108 is a deformable mirror. A deformable mirror can locally change the reflecting direction of light, and has been commercialized in various forms. FIG. 2B shows a cross-section of the deformable mirror. The deformable mirror includes a deformable membrane mirror surface 129 which reflects the incident light 126, a base portion 128, actuators 130 arranged between them, and a support portion (not shown) which circumferentially supports the mirror surface 129. Operating principles for the actuator 130 include those using an electrostatic force, magnetic force, and piezoelectric effect. The actuator 130 varies in arrangement depending on the operating principle to be used. A plurality of actuators 130 are two-dimensionally arrayed on the base portion 128.

Selectively driving the actuators 130 can freely deform the mirror surface 129. In general, a deformable mirror includes several tens (10) to several hundreds (100) of actuators. Referring back to FIG. 1, a scanning optical system 109 one-dimensionally or two-dimensionally scans the light reflected by the reflecting mirrors 107c and 107d. In this embodiment, the scanning optical system 109 uses two galvano scanners for main scanning (horizontal direction of fundus) and sub-scanning (vertical direction of fundus). For high-speed imaging, however, a resonant scanner may be used on the main scanning side of the scanning optical system 109. Depending on the arrangement, it is possible to use optical elements such as a mirror and lens between the respective scanners in the scanning optical system 109 to set the respective scanners in an optically conjugate state.

The measurement light 105 scanned by the scanning optical system 109 irradiates an eye 111 through eyepiece lenses 110a and 110b. The measurement light 105 which has irradiated the eye 111 is reflected or scattered by the fundus. Adjusting the positions of the eyepiece lenses 110a and 110b makes it possible to optimally irradiate the eye 111 with light in accordance with its visibility. Although an eyepiece lens 110 is used as an eyepiece, it is possible to use a spherical mirror or the like.

The reflected or scattered light from the retina of the eye 111 propagates backward along the same path as that of the incident light. The light splitting unit 106 then reflects part of the light to the wavefront sensor 115 to be used for the measurement of the wavefront of the reflected light. This embodiment uses a Shack-Hartmann sensor as the wavefront sensor 115.

The Shack-Hartmann sensor will be described with reference to FIGS. 3A to 3C. A light beam 131 is a light beam for the measurement of a wavefront, which is focused on a focal plane 134 on a CCD sensor 133 through a microlens array 132.

FIG. 3B shows a state observed from the position indicated by A-A in FIG. 3A. FIG. 3B shows how the microlens array 132 is constituted by a plurality of microlenses 135. The light beam 131 is focused on the CCD sensor 133 through the microlenses 135. For this reason, the light beam 131 is focused upon being split into spots equal in number to the microlenses 135.

FIG. 3C shows how the light beam 131 is focused on the CCD sensor 133. The light beam 131 passing through the microlenses 135 is focused into spots 136. The wavefront of the incident light beam 131 is then calculated from the positions of the spots 136.

Figure 4A:
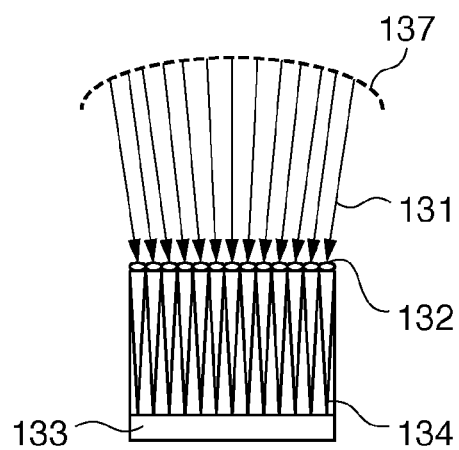
FIG. 4A is a view showing the measurement of a wavefront having spherical aberration.
Figure 4B:
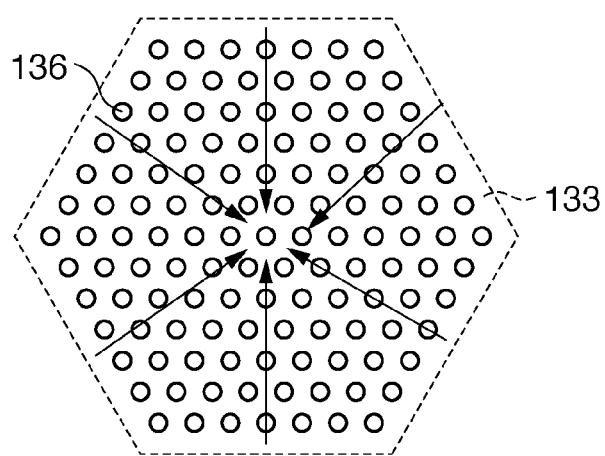
FIG. 4B is a view showing the focusing state of a CCD sensor 133.

A case in which a wavefront having spherical aberration is measured will be described with reference to FIG. 4A. The light beam 131 has a wavefront 137. The microlens array 132 focuses the light beam 131 at positions in a local tangential direction of the wavefront 137. FIG. 4B shows the focusing state of the CCD sensor 133. Since the light beam 131 has spherical aberration, the spots 136 are focused so as to be unevenly distributed to the central portion. Calculating these positions can analyze the wavefront 137 of the light beam 131.

This embodiment uses a Shack-Hartmann sensor as the wavefront sensor 115. However, the present invention is not limited to this, and may use another wavefront measurement method such as a curvature sensor or a method of obtaining a wavefront from focused point images by inverse calculation. The light splitting unit 104 reflects part of the reflected light transmitted through the light splitting unit 106. The light reflected by the light splitting unit 104 is guided to a light intensity sensor 114 through the collimator 112 and an optical fiber 113. The light intensity sensor 114 converts the light into an image signal. A control unit 117 then forms the image signal into an image as a fundus image, and displays it on a display 118.

The wavefront sensor 115 is connected to an adaptive optical control unit 116, and transfers a received wavefront to the adaptive optical control unit 116. The wavefront correction device 108 is also connected to the adaptive optical control unit 116, and performs modulation instructed by the adaptive optical control unit 116. Based on the wavefront acquired from the wavefront sensor 115, the adaptive optical control unit 116 calculates a modulation amount (correction amount) for correcting the wavefront into a wavefront without aberration, and issues a command to perform corresponding modulation to the wavefront correction device 108. This apparatus performs feedback control to always keep an optimal wavefront by repeatedly performing wavefront measurement and issuing an instruction to the wavefront correction device.

As described above, it is possible to allow the wavefront sensor 115 to measure aberration occurring at the eye 111 by setting the pupil of the eye 111, the wavefront correction device 108, the wavefront sensor 115, and the collimator 112 in an optically conjugate relation in advance. As a consequence, the wavefront correction device 108 allows efficient aberration correction. If they are set in an ideal conjugate relation, performing correction so as to reduce the aberration measured by the wavefront sensor 115 will improve the coupling efficiency between the collimator 112 and the optical fiber 113. This improves the efficiency of acquiring captured signals.

However, the path from the eye 111 to the collimator 112 differs in aberration from the path from the eye 111 to the wavefront sensor 115 in a strict sense. For this reason, the wavefront sensor 115 and the collimator 112 are not often in an optically conjugate state in a strict sense. In addition, since the collimator 112 itself has aberration, even if incident light on the collimator 112 exhibits no aberration, this state does not necessarily match the highest coupling efficiency for the optical fiber 113. In addition, in some cases, when stray light other than the measurement light 105 strikes the wavefront sensor 115, the accuracy of aberration measurement may degrade to result in insufficient aberration correction. Due to such various factors, the measurement result obtained by the wavefront sensor 115 may not correlate to the efficiency of coupling to the optical fiber 113.

Figure 5:
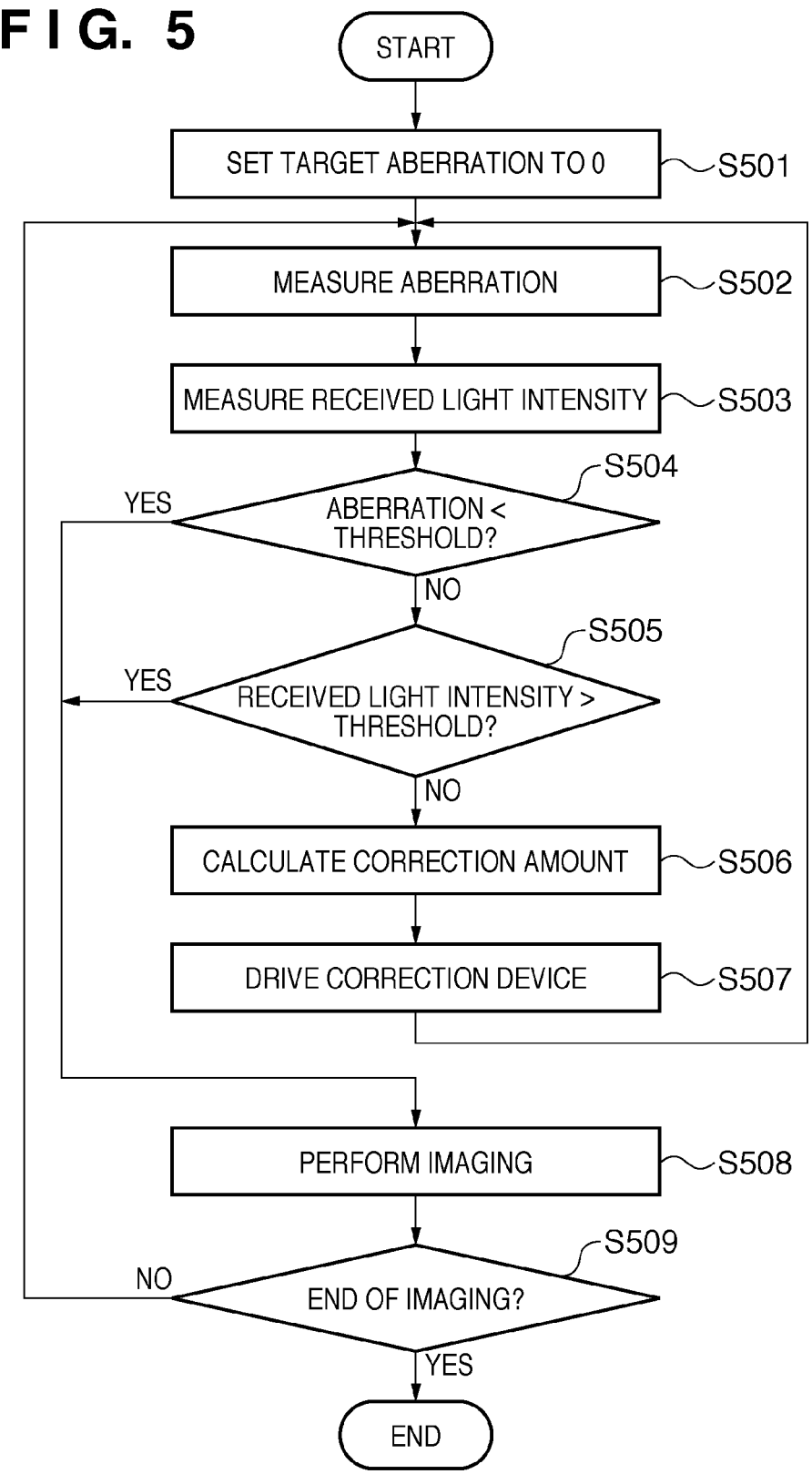
FIG. 5 is a flowchart showing a control procedure according to the first embodiment.

With regard to the above problems, a control procedure according to the first embodiment will be described with reference to the flowchart shown in FIG. 5. Note that alignment and the like for the eye 111 have been completed, and control has started from a state in which the measurement light 105 is applied.

In step S501, a target aberration is set to 0. That is, settings are made to minimize the aberration measured by the wavefront sensor 115. In step S502, the wavefront sensor 115 measures aberration originating from the shape or the like of an eye to be examined. This embodiment uses the intensity of a light reception signal as an image quality evaluation target. In step S503, the light intensity sensor 114 measures the intensity of light which it receives through the optical fiber 113 (intensity measurement processing).

In step S504, the adaptive optical control unit 116 obtains an aberration amount from the aberration measured in step S502 and determines whether the obtained aberration amount is smaller than a reference value (threshold) (aberration determination processing). The threshold may be a value unique to the apparatus or may be set by the person who performs imaging. The aberration amount in this embodiment indicates the total amount of disturbance of the wavefront obtained from the obtained aberration, but may be the total amount of deviation from a reference wavefront (flat wavefront) or the like. If the adaptive optical control unit 116 determines that the aberration amount is smaller than the threshold (YES in step S504), the process advances to step S508. If the adaptive optical control unit 116 determines that the aberration amount is equal to or more than the threshold (NO in step S504), the process advances to step S505.

In step S505, the adaptive optical control unit 116 executes reflected light evaluation, that is, determines whether the light intensity measured in step S503 is higher than a preset reference value (threshold) (intensity determination processing). In this case, the threshold is a value unique to the apparatus.

The operator can designate a ratio to the maximum received light intensity assumed at the time of the use of the apparatus, and a threshold is set from the designated value. Note that the person who performs imaging may arbitrarily set a threshold. If the adaptive optical control unit 116 determines that the light intensity is higher than the threshold (YES in step S505), since the corresponding state allows imaging, the process advances to step S508. If the adaptive optical control unit 116 determines that the light intensity is equal to or less than the threshold (NO in step S505), the process advances to step S506. In step S506, the adaptive optical control unit 116 calculates a correction amount based on the measurement result. In step S507, a correction device 508 is driven under the control of the adaptive optical control unit 116. The process then returns to step S502. The adaptive optical control unit 116 repeats this processing until the condition in step S504 or S505 is satisfied.

In step S508, the apparatus performs imaging. In step S509, adaptive optical control unit 116 determines whether to terminate the processing. If the adaptive optical control unit 116 determines not to terminate the processing (NO in step S509), the process returns to step S502. If the adaptive optical control unit 116 determines to terminate the processing (YES in step S509), the adaptive optical control unit 116 terminates the processing. Note that in the above procedure, imaging processing and aberration correction processing are sequentially performed, but it is possible to perform control to perform them concurrently.

The transitions of an aberration amount and received light intensity at the time of aberration correction will be described with reference to FIGS. 6A to 6D. Referring to each of FIGS. 6A to 6D, the abscissa represents the elapsed time from the start of aberration correction, the left ordinate represents the measured aberration amount, and the right ordinate represents the received light intensity. The solid line indicates changes in measured aberration amount, and a broken line 141 indicates changes in received light intensity. Received light intensities are sequentially recorded in this manner.

FIG. 6A shows changes in measured aberration amount and received light intensity in an apparatus having an ideal aberration correction function. A measured aberration amount 140 decreases with progress in feedback control for aberration correction, and reaches the limit of correction and converges at a given point 142a. On the other hand, a received light intensity 141 increases with progress in feedback control for aberration correction because the influence of aberration decreases. The received light intensity also reaches its peak at a point 142b at the same time as the point 142a at which aberration correction converges. Maintaining the correction state in this state will maintain the measured aberration amount at almost the same aberration amount as that at the point 142a and also maintain the received light intensity 141 at almost the same intensity as that at the point 142b. Performing imaging in this state can implement imaging with high image quality.

FIG. 6B shows an example of changes in measured aberration amount and received light intensity in an apparatus having a general aberration correction function. A measured aberration amount 140 decreases with progress in feedback control for aberration correction, and reaches the limit of correction and converges at a given point 142a. On the other hand, a received light intensity 141 increases with progress in feedback control for aberration correction because the influence of aberration decreases. In this case, even in a state in which the aberration measured by the wavefront sensor 115 is small, the received light intensity does not become maximum and decreases from the maximum value of a point 142b due to the influence of stray light to the wavefront sensor 115, aberration existing at the light-receiving unit, the disturbance of the optical conjugate relation between the wavefront sensor 115 and the light-receiving unit, and the like. At the point 142a at which the measured aberration amount converges to a small value, the received light intensity is at the value indicated by a point 142c, which is lower than the intensity at the point 142b which is the maximum received light intensity. In this state, the apparatus may not exhibit its original performance.

FIG. 6C shows changes in measured aberration amount and received light intensity according to this embodiment. When feedback control for aberration correction starts, a measured aberration amount 140 decreases, and a received light intensity 141 increases, as in the case shown in FIG. 6A. The received light intensity 141 increases and reaches a preset threshold 143 for received light intensity at a given time point 144. Since this state matches the condition in step S505 in FIG. 5, the feedback control is stopped at the time point 144, and the corrected state is maintained. It is possible to maintain the received light intensity 141 and the measured aberration amount 140 at the values at the time point 144 at which the feedback control is stopped, even though they slightly vary depending on the state of the eye and the state of the apparatus. This makes it possible to perform imaging with high received light intensity.

This embodiment uses a received light intensity as an image quality evaluation result, which is used as a determination condition for the completion of aberration correction. It is, however, possible to use the contrast (contrast ratio), resolution, or the like of an acquired image as an image quality evaluation result to be used as a determination condition.

As described above, this embodiment can execute proper aberration correction in accordance with the imaging state, and can implement fundus imaging with high image quality. Note that FIG. 6D will be described later.

(Second Embodiment)

Another example of processing to be performed when the present invention is applied to scanning laser ophthalmoscope (SLO) will be described next.

Figure 7:
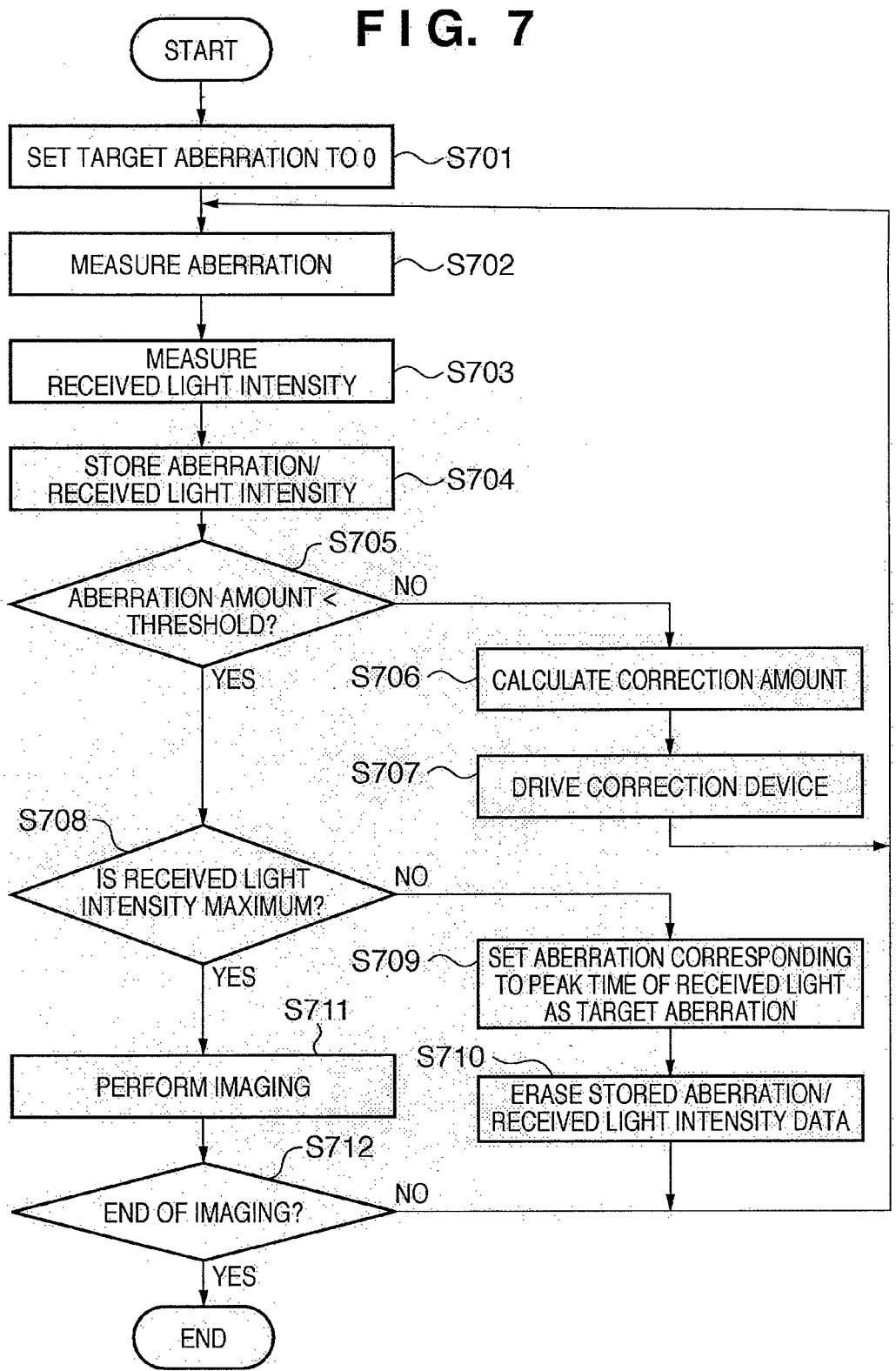
FIG. 7 is a flowchart showing a control procedure according to the second embodiment.

The arrangement of the apparatus according to the second embodiment is the same as that in the first embodiment, which is shown in the schematic view of FIG. 1. A control procedure according to this embodiment will be described with reference to the flowchart of FIG. 7. The second embodiment is configured to implement an optimal corrected state by performing control in accordance with the maximum received light intensity obtained in the process of aberration correction instead of determining a threshold for received light intensity in advance in the manner described in the first embodiment.

First of all, in step S701, this apparatus performs control so as to minimize the aberration measured by a wavefront sensor 115 upon setting the target aberration for aberration correction to 0. This embodiment performs aberration correction processing by managing aberration using a Zernike polynomial, and hence sets each coefficient of the Zernike polynomial to 0 as an aberration target. The apparatus then executes a basic adaptive optical procedure.

In step S702, the wavefront sensor 115 measures an aberration. In step S703, a light intensity sensor 114 measures the intensity of light which it receives through an optical fiber 113.

In step S704, a storage unit (not shown) stores the information of the aberration measured in step S702 and the information of the received light intensity measured in step S703.

Aberration information and received light intensity information are managed in pairs. Aberration information includes each coefficient of a Zernike polynomial indicating an aberration. The information to be stored may be the measurement history of aberration information and received light intensity information from the start of aberration correction or aberration information and received light intensity information at a time point when the received light intensity is maximum.

In step S705, an adaptive optical control unit 116 determines whether the aberration amount measured in step S702 is smaller than a preset reference value (threshold). The threshold may be a value unique to the apparatus or may be set by the person who performs imaging. In this case, if a new target aberration is set in step S709 (to be described later), a new reference value (threshold) is set based on the set target aberration. If the adaptive optical control unit 116 determines that the aberration amount is equal to or more than the threshold (NO in step S705), the process advances to step S706. If the adaptive optical control unit 116 determines that the aberration amount is smaller than the threshold (YES in step S705), the process advances to step S708.

In step S706, the adaptive optical control unit 116 calculates a correction amount based on the measurement result.

In step S707, the apparatus drives a wavefront correction device 108 to set the aberration to the target aberration, that is, 0, under the control of the adaptive optical control unit 116. The process then returns to step S702.

In step S708, the adaptive optical control unit 116 executes image quality evaluation, that is, compares the received light intensity at this time point with the received light intensity history stored in the storage unit (not shown) to determine whether the received light intensity at the time point is the maximum value among the received light intensities measured from the start of the aberration correction. If the adaptive optical control unit 116 determines that the received light intensity at the time point is the maximum value (YES in step S708), the process advances to step S711. If the adaptive optical control unit 116 determines that the received light intensity at the time point is not the maximum value (NO in step S708), the process advances to step S709. Note that in this procedure, the adaptive optical control unit 116 determines in step S708 whether the received light intensity at the time point is the maximum value among the received light intensities measured from the start of the aberration correction. In this determination step, however, if the received light intensity falls within a predetermined range from the maximum value, instead of being the maximum value, the process may advance to step S711.

In step S709, the aberration information at the time point corresponding to the maximum received light intensity, which is stored in the storage unit (not shown), is set as a new target aberration for aberration correction. In step S710, the aberration information and received light intensity stored in the storage unit (not shown) are erased. The process then returns to step S702.

After the process returns to step S702, the same processing as that described above is repeated except that the target aberration is updated. Since the aberration at the time point corresponding to almost the maximum received light intensity is designated as a target aberration, making the aberration correction converge to a value near the target aberration will achieve a high received light intensity.

In step S711, the apparatus executes imaging processing. In step S712, the apparatus determines whether to terminate the processing. Upon determining to terminate the processing, based on an end request or the like (YES in step S712), the apparatus terminates the processing. If the apparatus determines not to terminate the processing (NO in step S712), the process returns to step S702.

Changes in aberration amount and received light intensity will be described next with reference to FIGS. 6A to 6D. FIGS. 6A, 6B, and 6C are the same as those described in the first embodiment, and hence a description of them will be omitted.

FIG. 6D shows changes in aberration amount and received light intensity according to the second embodiment. When feedback control for aberration correction starts, a measured aberration amount 140 decreases, and a received light intensity 141 increases, in the same manner as described with reference to FIG. 6B. The received light intensity 141 increases, and takes the maximum value at a given time point 145. After the time point 145, as the correction proceeds, that is, the time elapses, the received light intensity 141 decreases. The measured aberration amount 140 keeps decreasing, and converges to a sufficiently small value at a time point 146, thus satisfying the determination condition in step S705. At the time point 146, the received light intensity 141 has already decreased, as indicated by a point 142c. Since the aberration amount is smaller than the threshold (YES in step S705), the process advances to step S708. In step S708, the apparatus compares the stored received light intensity information with the received light intensity information at the time point 146. Since the received light intensity indicated by the point 142c at the time point 146 is lower than the received light intensity indicated by a point 142b at the time point 145 at which the received light intensity 141 becomes maximum (NO in step S708), the process advances to step S709. In step S709, the apparatus sets, as a target aberration, the aberration indicated by the point 142b at the time point 145 at which the received light intensity 141 becomes maximum. In step S710, the apparatus clears the stored information. The process then returns to step S702 to continue the aberration correction processing.

With the subsequent aberration correction processing, the received light intensity 141 increases, and the measured aberration amount 140 increases. At a time point 147, the aberration almost coincides with the target aberration, and the aberration correction converges. The process then advances to step S708 through the determination processing in step S705. In step S708, the apparatus compares the received light intensity at the time point 147 with the stored information. If the apparatus determines that the received light intensity at the time point 147 is maximum (YES in step S708), the process advances to step S711 to perform imaging. At the time point 147, the aberration amount has increased to an amount similar to the value at the time point 145, but the received light intensity 141 has increased to an intensity similar to that at the time point 142b. It is therefore possible to perform imaging with high image quality. If the apparatus determines in step S708 that there is a time point at which a higher received light intensity appears (NO in step S708), the apparatus repeats the same processing based on the aberration information at that time point. This makes it possible to perform imaging with almost the highest received light intensity.

Like the first embodiment, the second embodiment may set a determination criterion by using the contrast (contrast ratio) or resolution of an acquired image as an image quality evaluation target. In addition, the above procedure may include the processing of executing aberration correction by using several types of shapes, such as a spherical shape and a cylindrical shape, as target aberrations, and checking received light intensities in the process of the execution, in order to detect a state in which the received light intensity is high.

As described above, this embodiment can perform aberration correction to achieve a state in which the received light intensity is maximum, and can implement fundus imaging with high image quality regardless of an imaging state.

(Third Embodiment)

The following is an example of applying the present invention to optical coherent tomography (OCT).

Figure 8:
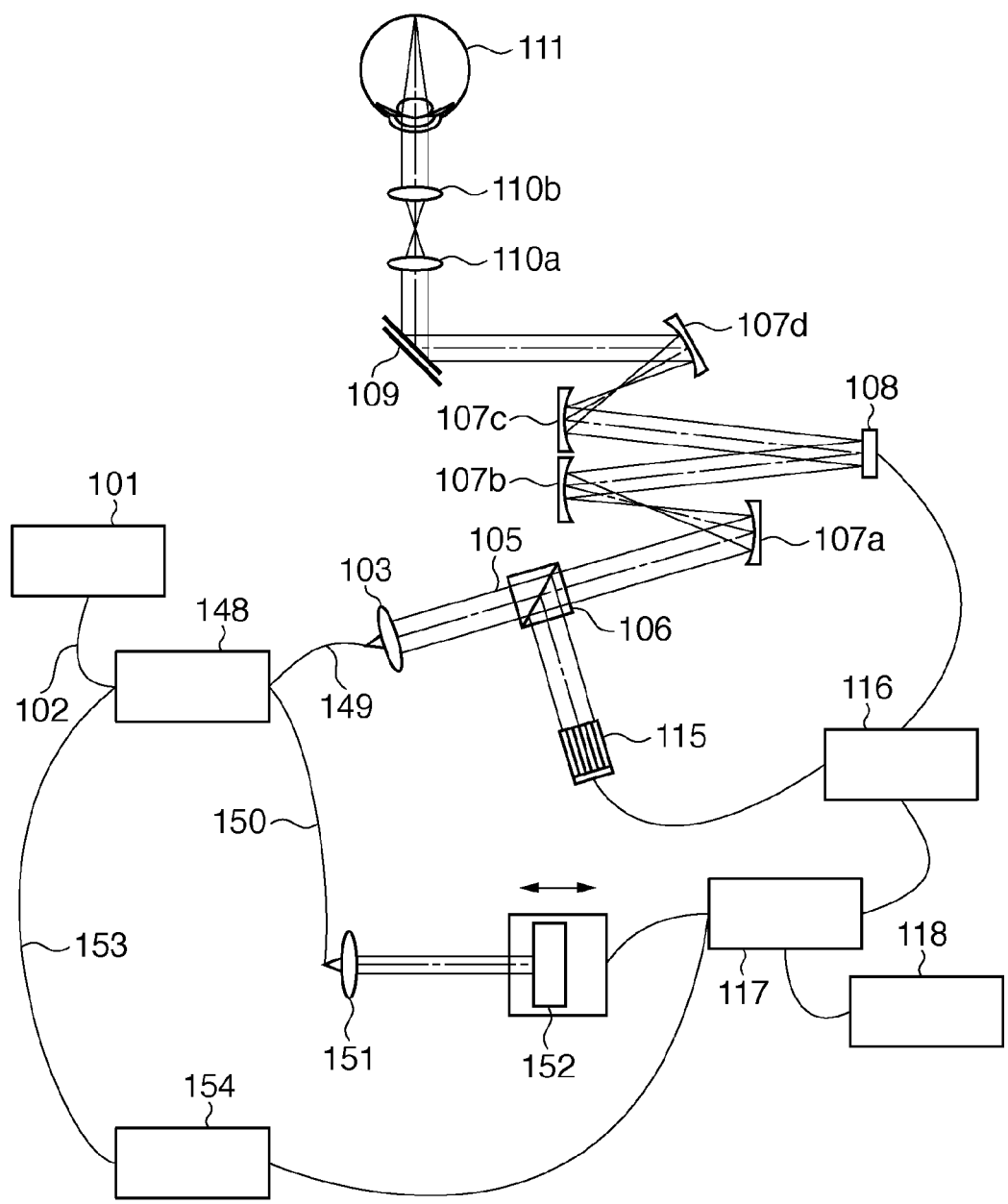
FIG. 8 is a view for explaining OCT according to the third embodiment.

An example of a fundus imaging apparatus will be described with reference to FIG. 8. A light source 101 is an SLD light source with a wavelength of 840 nm. The light source 101 may be a low-coherence SLD with a wavelength width of 30 nm or more. Alternatively, the light source 101 may be an ultrashort pulse laser such as a titanium-sapphire laser.

The light emitted from the light source 101 is guided to a fiber coupler 148 through a single-mode optical fiber 102. The fiber coupler 148 splits the light emitted from the light source 101 into a light beam to a measurement light path 149 and a light beam to a reference light path 150. This apparatus is configured to use a fiber coupler with a branching ratio of 10:90 to guide 10% of the amount of incident light to the measurement light path 149, and 90% of the amount of incident light to the reference light path 150. A collimator 103 collimates the light passing through the measurement light path 149 and outputs it as collimated measurement light. The arrangement after the collimator 103 is the same as that described in the first embodiment. The light passing through the measurement light path 149 irradiates an eye 111 through the adaptive optical system and the scanning optical system. The reflected light from the eye 111 is guided to the measurement light path 149 and reaches the fiber coupler 148.

The reference light passing through the reference light path 150 emerges from a collimator 151. This light is reflected by an optical path length changing unit 152 and then returns to the fiber coupler 148.

The measurement light and reference light reaching the fiber coupler 148 are multiplexed. The resultant light is then guided to a spectroscope 154 through an optical fiber 153. A control unit 117 forms a tomogram of the fundus based on coherent light information having undergone spectroscopy by the spectroscope 154. Making the control unit 117 control the optical path length changing unit 152 can acquire an image at a desired depth position. As in the first embodiment, this apparatus causes the wavefront sensor 115 to measure a wavefront, and then drives a wavefront correction device 108 to cancel the wavefront aberration.

Like the first or second embodiment, the third embodiment performs aberration correction by using, as a determination criterion, a received light intensity which is one of image quality evaluation targets. In this embodiment, since the spectroscope 154 receives light, spectrally-resolved information is acquired. It is possible to use, as a received light intensity, the result obtained by adding pieces of spectrally-resolved information or the coherent signal measured by the spectroscope 154.

Performing the processing shown in FIG. 5 or FIGS. 6A to 6D can implement imaging with an almost maximum received light intensity in this embodiment as well. Like the first embodiment, this embodiment may use the contrast or resolution of an acquired image as a determination criterion instead of a received light intensity.

As described above, this embodiment can perform aberration correction to achieve a state of a high received light intensity in OCT as well, and can implement fundus imaging with high image quality regardless of an imaging state.

(Fourth Embodiment)

The above embodiments each have exemplified the arrangement configured to measure an aberration and perform correction by using the aberration measurement result. However, it is not always necessary to measure an aberration. For example, the present invention may have an arrangement configured to evaluate the sharpness of a captured image based on the luminance value or the like of the image and perform control based on the evaluation result to drive a correction device so as to make the image to be finally output have higher sharpness. In this case, it is possible to control the correction device by using a light reception result (so as to set the intensity of received return light to a predetermined value or more) instead of measuring an aberration. Note that the present invention may have an arrangement configured to measure an aberration and control the correction device by using both the measurement result and a light reception result.

According to the present invention, it is possible to execute aberration correction in accordance with an imaging state and implement fundus imaging with high image quality.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-166502 filed on Jul. 23, 2010, which is hereby incorporated by reference herein in its entirety.

What is claimed is:

1. An ophthalmic apparatus comprising:
   an aberration measurement unit arranged to measure aberration of an eye to be examined by using a return light from the eye having been irradiated by an irradiating light;
   an aberration correction unit arranged to correct the aberration of the eye;
   a light-receiving unit arranged to receive the return light from the eye;
   an intensity measurement unit arranged to measure the intensity of the return light received by said light-receiving unit; and
   a control unit arranged to control said aberration correction unit based on a measurement result obtained by said aberration measurement unit and the intensity of the return light measured by said intensity measurement unit; and
   an image generating unit arranged to generate an image of the eye on the basis of the return light received by said light receiving unit via the aberration correction unit.

2. The apparatus according to claim 1, further comprising:
   a conversion unit arranged to convert the return light received by said light-receiving unit into an image signal, wherein said intensity measurement unit is arranged to measure the image signal converted by said conversion unit, and wherein said control unit is arranged to control said aberration correction unit based on the intensity measurement result obtained by said intensity measurement unit and the measurement result obtained by said aberration measurement unit.

3. The apparatus according to claim 1, wherein said light-receiving unit is arranged to receive, as the return light, the irradiating light which is scanned on the eye and reflected at different positions on the eye, wherein said apparatus further comprises a contrast ratio measurement unit arranged to measure contrast ratios of the return light reflected at the different positions on the eye, and wherein said control unit is arranged to control said aberration correction unit based on the measurement result obtained by said contrast ratio measurement unit and the aberration measured by said aberration measurement unit.

4. The apparatus according to claim 1, wherein said control unit is arranged to control said aberration correction unit so as to maintain a corrected state set upon correction by said aberration correction unit based on the intensity measurement result obtained by said intensity measurement unit and the aberration measured by said aberration measurement unit.

5. The apparatus according to claim 1, wherein said control unit is arranged to control said aberration correction unit based on an aberration at a time point at which the measurement result of the intensity of the return light is maximum in a case where the aberration measured by said aberration measurement unit is a predetermined aberration.

6. The apparatus according to claim 1, wherein said control unit is arranged to control said aberration correction unit so as to set an aberration target based on the intensity measurement result obtained by said intensity measurement unit and to set the aberration measured by said aberration measurement unit to the set aberration target.

7. The apparatus according to claim 1, wherein said control unit controls said aberration correction unit so as to make said aberration correction unit start correcting an aberration when alignment for the eye is complete.

8. A control method for an ophthalmic apparatus, the method comprising:

an aberration measurement step of causing a measurement unit to measure aberration of an eye to be examined by using a return light from the eye having been irradiated by an irradiating light;

an aberration correction step of causing an aberration correction unit to correct the aberration of the eye;

a light-receiving step of of causing a light-receiving unit to receive the return light from the eye;

an intensity measurement step of causing an intensity measurement unit to measure the intensity of the return light received in said light-receiving step;

a control step of causing a control unit to control said aberration correction step based on a measurement result obtained in said aberration measurement step and the intensity of the return light measured in said intensity measurement step; and an image generating step of causing an image generating unit to generate an image of the eye on the basis of the return light received by said light receiving unit via the aberration correction unit.

9. A non-transitory apparatus-readable storage medium storing a program that causes an apparatus to execute the control method for an ophthalmic apparatus as claimed in claim 8.

10. An ophthalmic apparatus comprising:

an aberration measurement unit arranged to measure aberration of an eye to be examined by using a return light from the eye having been irradiated by an irradiating light;

an aberration correction unit arranged to correct the aberration of the eye;

a light receiving unit arranged to receive the return light from the eye;

an intensity measurement unit arranged to measure the intensity of the return light received by said light receiving unit; and a control unit arranged to control said aberration correction unit based on a measurement result obtained by said aberration measurement unit and the intensity of the return light measured by said intensity measurement unit, wherein in a case where (a) the aberration amount is not smaller than a first threshold and (b) the intensity of the return light received by said light-receiving unit is higher than a second threshold, said apparatus performs imaging.

11. An ophthalmic apparatus comprising:

an aberration measurement unit arranged to measure aberration of an eye to be examined by using a return light from the eye having been irradiated by an irradiating light;

an aberration correction unit arranged to correct the aberration of the eye;

a light receiving unit arranged to receive the return light from the eye;

an intensity measurement unit arranged to measure the intensity of the return light received by said light receiving unit; and a control unit arranged to switch between a first mode in which the aberration correction unit is controlled based on the intensity measured by said intensity measurement unit and the aberration measured by said aberration measurement unit, and a second mode in which said aberration correction unit is controlled based on the aberration measured by said aberration measurement unit regardless of the intensity measured by said intensity measurement unit.

12. The apparatus according to claim 11, wherein the control unit controls said aberration correction unit in the first mode in a case where the aberration measured by said aberration measurement unit is smaller than a predetermined threshold, and controls said aberration correction unit in the second mode in a case where the aberration measured by said aberration measurement unit is not smaller than the predetermined threshold.

13. An ophthalmic apparatus comprising:

an aberration measurement unit arranged to measure aberration of an eye to be examined by using a return light from the eye having been irradiated by an irradiating light;

a light receiving unit arranged to receive the return light from the eye;

an intensity measurement unit arranged to measure the intensity of the return light received by said light receiving unit;

a determination unit arranged to determine whether the intensity measured by said intensity measurement unit is not smaller than a second threshold, in a case where the aberration measured by said aberration measurement unit is not smaller than a first threshold; and an aberration correction unit arranged to correct the aberration of the eye, wherein said aberration correction unit corrects the aberration of the eye based on the aberration measured by said aberration measurement unit, in a case where said determination unit determines that the intensity measured by said intensity measurement unit is smaller than the second threshold.

14. The apparatus according to claim 13, further comprising an image capturing unit arranged to capture the eye, wherein said image capturing unit captures the eye in a case where said determination unit determines that the intensity measured by said intensity measurement unit is not smaller than the second threshold.

15. An ophthalmic apparatus comprising:

an aberration measurement unit arranged to measure aberration of an eye to be examined by using a return light from the eye having been irradiated by an irradiating light;

an aberration correction unit arranged to correct the aberration of the eye;

a light receiving unit arranged to receive the return light from the eye;

an intensity measurement unit arranged to measure the intensity of the return light received by said light receiving unit;

a storage unit arranged to store a control status of said aberration correction unit where the intensity measured by said intensity measurement unit is not less than a predetermined value;

a control unit arranged to control said aberration correction unit based on the control status stored in said storage unit; and an image generating unit arranged to generate an image of the eye on the basis of the return light received by said light receiving unit via the aberration correction unit.

* * * * *